(12) United States Patent
Schmid

(10) Patent No.: US 7,379,764 B2
(45) Date of Patent: May 27, 2008

(54) MEDICAL SENSOR

(75) Inventor: Alfons Schmid, Böblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 345 days.

(21) Appl. No.: 10/544,364

(22) PCT Filed: Feb. 2, 2004

(86) PCT No.: PCT/IB2004/000242

§ 371 (c)(1),
(2), (4) Date: Aug. 3, 2005

(87) PCT Pub. No.: WO2004/069047

PCT Pub. Date: Aug. 19, 2004

(65) Prior Publication Data

US 2006/0149149 A1 Jul. 6, 2006

(30) Foreign Application Priority Data

Feb. 5, 2003 (EP) .................................. 03100243

(51) Int. Cl.
*A61B 5/1455* (2006.01)
(52) U.S. Cl. ....................................... 600/344; 600/310
(58) Field of Classification Search ................ 600/310, 600/322, 323, 340, 344
See application file for complete search history.

(56) References Cited

U.S. PATENT DOCUMENTS

| | | | |
|---|---|---|---|
| 3,810,460 A | 5/1974 | Van Nie | |
| 4,109,643 A | 8/1978 | Bond et al. | |
| 4,685,464 A | 8/1987 | Goldberger et al. | |
| 5,054,488 A | 10/1991 | Muz | |
| 5,584,296 A * | 12/1996 | Cui et al. | 600/479 |
| 5,830,136 A * | 11/1998 | Delonzor et al. | 600/344 |
| 5,891,026 A | 4/1999 | Wang et al. | |
| 5,919,133 A | 7/1999 | Taylor et al. | |
| 6,745,061 B1 * | 6/2004 | Hicks et al. | 600/344 |

FOREIGN PATENT DOCUMENTS

| | | |
|---|---|---|
| DE | 37 03 458 C2 | 8/1988 |
| EP | 0 127 947 A2 | 12/1984 |
| WO | WO 92/21280 A1 | 12/1992 |

* cited by examiner

*Primary Examiner*—Eric F Winakur

(57) ABSTRACT

The present invention relates to a medical sensor (1) for measuring pulse, blood, tissue and/or skin parameters by means of electromagnetic waves in the transmission or reflection method. The sensor (1) has a strip- and/or band-shaped carrier part (2) which carries at least one transmitter element and at least one receiver element. In order that the sensor (1) can be used on a patient more than once and is sufficiently secured against relative movements with respect to a body part, the carrier part (2), on an inner side (9) provided to make contact with the body part, has at least two adhesive bodies (25, 26) which are spaced apart from one another and during measurement adhere to the body part, while the rest of the inner side (9) is designed to be essentially non-adhesive with respect to the body part.

17 Claims, 2 Drawing Sheets

MEDICAL SENSOR

Figure 1:
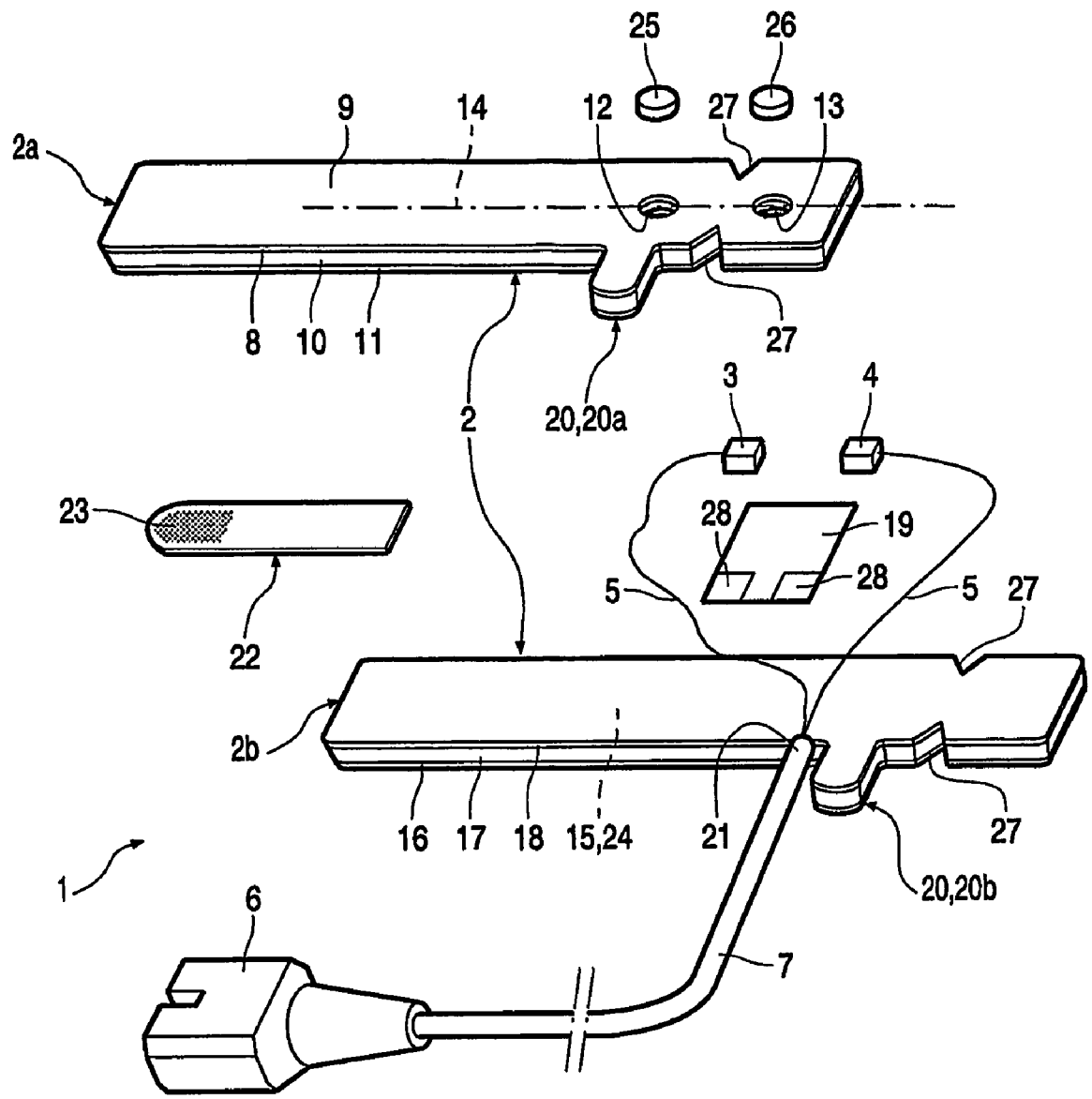

The present invention relates to a medical sensor for measuring pulse, blood, tissue and/or skin parameters by means of electromagnetic waves in the transmission or reflection method.

During an operation or during a stay in intensive care, it may be expedient to check and monitor, inter alia, the lung function, metabolism and heart rate of a patient. This may be carried out, for example, by measuring the oxygen saturation and the pulse rate. For this, sensors of the type mentioned above are used, by means of which a measurement, derived from the pulse, of the arterial oxygen saturation can be carried out using an optoelectronic transmission measurement or reflection measurement. Such a sensor usually comprises at least one transmitter, for example a light-emitting diode LED which can emit infrared light and an LED which can emit red light, and also at least one receiver, usually a photodiode. Furthermore, such a sensor comprises a carrier assembly which positions the transmitter and receiver in the desired manner on a body part of the patient, for example on the finger, toe, hand or foot.

With sensors, a distinction is made between single-use sensors, which can be used only once, semi-reusable sensors, in which a throwaway part can be replaced after each use, and reusable sensors, which can be used to carry out a number of measurements. With reusable sensors, a distinction can also be made between those which can be used for different patients one after the other and those which can be used a number of times but only for the same patient.

EP 0 127 947 B1 and U.S. Pat. No. 5,891,026 disclose sensors of the abovementioned type which in each case have a strip- or band-shaped carrier part which for the respective measurement is wound around the finger, toe, hand or foot.

In the case of the sensor disclosed in U.S. Pat. No. 5,891,026, the sensor is attached to the respective body part by means of a Velcro fastening (hook and loop fastening). An inner side of the carrier part, which bears against the respective body part, is in this case designed to be completely non-adhesive. By virtue of this design, this sensor can be used a number of times on the same patient. With this sensor, there is no direct fixing of the carrier part to the respective body part, so that in the event of voluntary or involuntary movements of the patient there is a risk that the carrier part will slip in relation to the body part and the measurements will be impaired as a result.

In the case of the sensor disclosed in EP 0 127 947 B1, an inner side of the carrier part, which bears against the respective body part, is designed in its entirety as an adhesive surface which fixes the carrier part directly to the body part. This sensor, which is also referred to as an adhesive sensor, is securely fixed to the body part for the respective measurement. However, such an adhesive sensor can be used only once. Furthermore, during removal of such an adhesive sensor from the respective body part, there is the risk of damage to the skin, in particular in the case of neonatal or geriatric patients.

U.S. Pat. No. 3,810,460 and U.S. Pat. No. 4,685,464 disclose sensors which are designed as clip sensors, the carrier part of which in each case has two legs mounted such that they can pivot in relation to one another about an axis of pivoting. These clip legs are prestressed in the closing direction by means of an appropriate spring, so that the clip sensor can be clipped, for example, to a finger in a self-retaining manner. Such sensors are relatively expensive to produce, so that they can be provided only as reusable sensors.

DE 37 03 458 C2 and U.S. Pat. No. 4,109,643 disclose further sensors which are designed as cuff sensors, the carrier part of which forms a sleeve which can be pushed onto the finger or toe. Such sleeve sensors are also relatively expensive to produce, so that they can only be provided as reusable sensors.

It is an object of the present invention to specify an improved embodiment for a medical sensor of the type mentioned above, which in particular allows multiple use on the same patient and is held on the respective body part in an improved manner.

This object is achieved according to the invention by the subject matter of the independent claim. Advantageous embodiments form the subject matter of the dependent claims.

The invention is based on the general concept of forming two or more locally defined adhesive zones on the inner side of the carrier part, which adhesive zones have increased friction and/or adhesion in relation to the body part compared with the rest of the inner side of the carrier part. In this context, the invention makes use of the knowledge that, for adequate attachment of the carrier part to the respective body part, it is sufficient to adhere the carrier part to more locations on the body part, said locations being spaced apart from one another. Since, according to the invention, it is not the entire inner side of the carrier part that is designed to be adhesive, the risk of damage to the skin when removing the sensor is reduced, even in the case of patients with sensitive skin. Furthermore, the sensor according to the invention does not become unusable upon removal from the body part, so that it can be used a number of times on the same patient.

In a further embodiment, two adhesive bodies for forming two adhesive zones may be provided, where a first adhesive body covers the at least one transmitter element while the second adhesive body covers the at least one receiver element. The two adhesive bodies are designed to be permeable to the electromagnetic waves used for measurement. This development is based on the knowledge that for the quality of the measurements it is of primary importance that transmitter and receiver do not change their relative position with respect to the body part, whereas relative movements of other components of the sensor have little or no influence on the measurements. Accordingly, this embodiment comprises only two adhesive bodies, one of which is positioned in the region of the transmitter and the other of which is positioned in the region of the receiver. In a particular embodiment, the at least one transmitter element may be arranged inside the carrier part, with a transmitter opening being made in the carrier part, through which transmitter opening the at least one transmitter element emits waves during measurement, the first adhesive body being arranged in this transmitter opening. In addition or as an alternative, the at least one receiver element may be arranged in the carrier part, with a receiver opening being made in the carrier part, through which receiver opening the at least one receiver element receives waves during measurement, the second adhesive body being arranged in this receiver opening. By virtue of this construction, the inner side of the carrier part can be designed to be particularly skin-friendly, so that the attached sensor in particular does not generate any uncomfortable pressure points. Furthermore, by virtue of this construction, the handling of the sensor is simplified, since its carrier part can be attached to the respective body part in a simpler manner.

The adhesive bodies may consist for example of a gel-like adhesive compound. As an alternative or in addition, the adhesive bodies may consist of an adhesive that is not hardened and does not harden during the service life of the sensor—if used correctly. By virtue of these configurations, it is possible to achieve for the adhesive bodies, in a particularly simple manner, an adhesive action which on the one hand ensures sufficiently secure fixing of the carrier part to the body part and on the other hand can be regularly removed from the respective body part without any damage to the skin.

Other important features and advantages of the invention emerge from the subclaims, the drawings and the associated description of the figures, which is given with reference to the drawings.

It will be understood that the features mentioned above and those that are yet to be mentioned below can be used not only in the combination indicated in each case but also in other combinations or on their own, without departing from the scope of the present invention.

The invention will be further described with reference to examples of embodiments shown in the drawings to which, however, the invention is not restricted. In the drawings, the same reference numerals refer to identical or functionally identical or similar components.

FIG. 1 schematically shows a perspective view of the individual parts of a sensor according to the invention.

Figure 2:
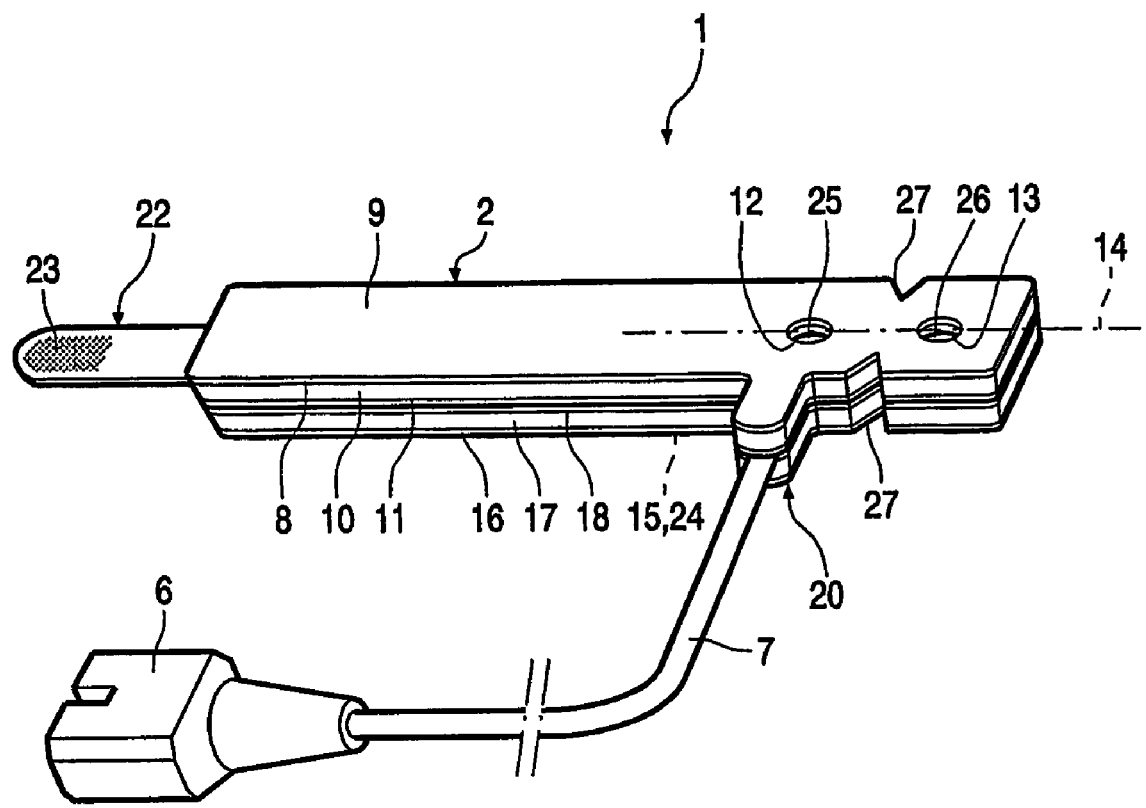

FIG. 2 schematically shows a perspective view of the sensor according to the invention in the assembled state.

As shown in FIG. 1, a medical sensor 1 according to the invention comprises a carrier part 2 which is designed in the shape of a strip or band. The sensor 1 is used to measure pulse, blood, tissue or skin parameters, where the sensor 1 operates using electromagnetic waves and in this case uses a transmission or reflection method. For this purpose, the carrier part 2 carries a transmitter unit 3, which comprises at least one transmitter element. The transmitter unit 3 usually comprises an LED that emits red light and an LED that emits infrared light. Furthermore, the carrier part 2 carries a receiver unit 4, which comprises at least one receiver element, preferably a photodiode. The transmitter unit 3 or its transmitter element and the receiver unit 4 or its receiver element are connected to a plug 6 via cables 5, the cables 5 being gathered together in a composite cable 7 outside the carrier part 2.

The carrier part 2 is constructed in a multilayer fashion. In order to be able to better illustrate the individual layers, these are shown on an over proportionally enlarged scale in the direction of their thickness in FIGS. 1 and 2.

As shown in FIG. 1, the carrier part 2 comprises an inner half 2a and an outer half 2b, which may be produced independently of one another. The inner half 2a in this case consists of a first textile layer 8 which forms an inner side 9 of the carrier part 2. This inner side 9, during use of the sensor 1, is applied to a body part of a patient, in particular to a finger, a toe or, in small patients, a foot or a hand. The first textile layer 8 consists, for example, of velour and is designed such that it essentially does not adhere to the body part, that is to say to human skin and hairs.

On the side facing away from the inner side 9, the first textile layer 8 is connected, in particular adhesively or thermally bonded, to a first layer of foamed material 10. The first layer of foamed material 10 consists, for example, of PE and is elastically compressible. In the embodiment shown here, a first adhesive film 11 is attached, in particular adhesively or thermally bonded, to the first layer of foamed material 10 on a side facing away from the inner side 9. The first adhesive film 11 has an adhesive coating on its side facing away from the inner side 9. Once the inner half 2a has been finished, this adhesive coating is covered with a peelable protective film, which is only peeled off for the purpose of assembling the sensor 1. In FIG. 1, this protective film has already been peeled off. The inner half 2a and its components, that is to say the first textile layer 8, the first layer of foamed material 10 and—where present—the first adhesive film 11, comprise a transmitter opening 12 and a receiver opening 13. The transmitter opening 12 and the receiver opening 13 are in each case arranged approximately on a longitudinal center line 14 of the carrier part 2 and are spaced apart from one another in the longitudinal direction of the carrier part 2.

The outer half 2b consists of a similar multilayer construction and comprises an outer side 15 of the carrier part 2, said outer side 15 facing away from the inner side 9 and being formed by a second textile layer 16. The second textile layer 16 may also consist essentially of a skin-friendly material, such as velour for example. On its side facing away from the outer side 15, the second textile layer 16 has a second layer of foamed material 17, which likewise consists of an elastically compressible foamed material, for example PE. Optionally, the second layer of foamed material 17 may have, on its side facing away from the outer side 15, a second adhesive film 18 which on its side facing away from the outer side 15 has an adhesive coating. The connections between the individual layers may also in this case be realized by adhesively bonded connections or thermally bonded connections. After production of the outer half 2b, the adhesive coating of the adhesive film 18 is expediently covered with an appropriate protective film which can be peeled off for assembly purposes, as in FIG. 1.

For assembly of the sensor 1, the transmitter unit 3, the receiver unit 4 and the cables 5 and 7 are then positioned. In order to obtain fixing of the composite cable 7 to the carrier part 2 with good tensile strength, a retaining plate 19 may be provided which is fitted to the outer part 2b and is fixedly attached to the end section 21 of the composite cable 7 remote from the plug 6. Adhesively bonded connections are also preferred here for attachment purposes. If the second adhesive film 18 is provided, the retaining plate 19 can simply be placed on the second adhesive film 18 at the appropriate location. The retaining plate 19 may also be provided with an adhesive layer which makes it possible to fix the end section 21 of the composite cable 7 to the retaining plate 19. The retaining plate 19 expediently has two tabs 28 which fold around the end section 21 for better fixing.

In order to further improve the fixing of the cables 5 and of the composite cable 7 to the carrier part 2, a projection 20 which sticks out to the side is formed on the carrier part 2, which projection 20 in this case likewise consists of an inner half 20a and an outer half 20b. The projection halves 20a and 20b are integrally formed on the carrier inner half 2a and on the carrier outer half 2b or on the components thereof. During assembly of the halves 2a, 2b of the carrier part 2, the end section 21 of the composite cable 7 with the tabs 28 of the retaining plate 19 is arranged between the halves 20a, 20b of the projection 20 and there adhesively and/or thermally bonded to the carrier part 2. As a result, effective strain relief of the optoelectronic components 3, 4 is achieved.

In the preferred embodiment shown here, the carrier part 2 is moreover equipped with a Velcro fastening 22, which has a hook element 23 having hooks and a loop element 24 having loops. The loop element 24 is in this case formed by an appropriate configuration of the outer side 15 of the carrier part 2, that is to say that an upper side of the second textile layer 16, which forms the outer side 15 of the carrier part 2, serves as a loop element 24 for the Velcro fastening 22. Such a Velcro fastening 22 may also be referred to as a hook and loop fastening.

In the embodiment shown here, the hook element 23 is designed as a tongue which upon assembly of the sensor 1 is arranged at an end section between the halves 2a, 2b of the carrier part 2. After assembly of the sensor 1, the hook element 23 is thus arranged at one end between the layers of foamed material 10, 17 or between the adhesive films 11, 18. As shown in FIG. 2, after assembly of the sensor 1, the hook element 22 projects in the longitudinal direction of the carrier part 2, beyond the textile layers 8, 16 thereof.

As shown in FIGS. 1 and 2, the sensor 1 according to the invention, on the inner side 9 of the carrier part 2, has at least two adhesive bodies 25, 26. In the preferred embodiment shown here, precisely two such adhesive bodies are provided, and these will be referred to below as the first adhesive body 25 and the second adhesive body 26. The adhesive bodies 25, 26 are spaced apart from one another and thereby form two locally defined adhesive zones within the inner side 9 of the carrier part 2, which inner side 9 is designed to be non-adhesive per se. The adhesive bodies 25, 26 are in this case dimensioned and positioned such that in the assembled state the first adhesive body 25 covers the transmitter unit 3 while the second adhesive body 26 covers the receiver unit 4. In order not to impair the operability of the optoelectronic components of the transmitter unit 3 and of the receiver unit 4, the adhesive bodies 25, 26 are made of a material which is permeable to the electromagnetic waves that are emitted by the transmitter elements of the transmitter unit 3.

The adhesive bodies 25, 26 consist, for example, of a gel-like adhesive. This adhesive may be designed, for example, such that it is not completely hardened when it forms the adhesive bodies 25, 26 and such that it also does not harden during the entire predetermined service life of the sensor 1 provided that the sensor 1 is not exposed to unacceptable environmental conditions. In this way, the sensor 1 can be used on the same patient almost as often as desired. This patient-related reusability of the sensor 1 is aided by the Velcro fastening 22, which can likewise be opened and closed almost as often as desired.

During application of the sensor 1, the carrier part 2 thereof is wound around the respective body part of the patient. If the sensor 1 operates in accordance with the transmission method, the carrier part 2 is attached to the body part such that transmitter unit 3 and receiver unit 4 lie opposite one another on opposite sides of the body part. The adhesive bodies 25, 26 then come to rest on the body part and by virtue of their adhesion at the measurement location produce adequate fixing of the carrier part 2 to the body part.

In order to be able to carry out optimal measurement of the pulse rate, it is desired that the carrier part 2 bears against the body part with a slight pressure. In the case of the sensor 1 according to the invention, the carrier part 2 is designed to be elastically compressible in the direction of its thickness. This is achieved in this case by the correspondingly compressible layers of foamed material 10, 17. The compressibility of the carrier part 2 is designed such that the carrier part 2, during application to the respective body part, can be compressed to the extent that resulting restoring forces press the inner side 9 of the carrier part 2 against the body part. Upon winding around the respective body part, a prestressed bearing of the carrier part 2 on the body part is thus generated, which prestressing can be fixed with the aid of the Velcro fastening 22.

In order to be able to wind the multilayer carrier part 2 in a particularly simple manner such that transmitter element 3 and receiver element 4 can be positioned on opposite sides of the body part, in accordance with the embodiment shown here the carrier part 2 may have lateral notches 27 that lie opposite one another and are arranged in the center, with respect to the longitudinal direction of the carrier part 2, between transmitter element 3 and receiver element 4. The notches 27 are V-shaped and run inward to form a point. The notches 27 may be formed during production of the halves 2a, 2b of the carrier part 2, so that the carrier part halves 2a, 2b or their layers 8, 10, 11 and 16, 17, 18 are accordingly provided with the notches 27.

As can be seen particularly clearly in FIG. 2, the first adhesive body 25 is preferably inserted in the transmitter opening 12, with the first adhesive body 25 expediently completely filling the transmitter opening 12. In this embodiment, in a corresponding manner, the second adhesive body 26 is inserted in the receiver opening 13 and expediently dimensioned such that it completely fills the receiver opening 13. The adhesive bodies 25, 26 may be designed such that they adhere to the transmitter element 3 and to the receiver element 4, respectively. The adhesive bodies 25, 26 may consist, for example, of a gel-like adhesive compound which is poured into the openings 12, 13 during production of the sensor 1. This adhesive compound then solidifies or hardens to a defined extent, with the adhesive compound being designed such that, on the inner side 9 of the carrier part 2, it has a surface which adheres at least to human skin. In order to be able to transport the finished sensor 1, it is expedient to apply a peelable protective film (not shown) to the inner side 9 of the carrier part 2 also in the region of the adhesive bodies 25, 26. This protective film may then be removed directly before use of the sensor 1.

On account of the arrangement of the optoelectronic components 3, 4 of the sensor 1 between the carrier part halves 2a, 2b, following assembly of the sensor 1 the transmitter unit 3 and the receiver unit 4 are housed in a protected manner inside the carrier part 2.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical sensor for measuring pulse, blood, tissue and/or skin parameters by means of electromagnetic waves in the transmission or reflection method, comprising:
   a band-shaped carrier part including:
      an upper half having a textile layer and a foam layer, the upper half defining first and second ports extending through the textile and foam layers,
      a lower half attached to the upper half;
   at least one transmitter element and at least one receiver element mounted on a retaining element, the retaining element being secured between the upper and lower halves with the transmitter element aligned with the first port and the receiver element aligned with the second port;
   first and second adhesive bodies filling the first and second ports covering the transmitter element and the receiver element, the adhesive bodies being permeable by waves emitted by the transmitter element, being a gel-like substance which does not harden during the service life of the sensor and during measurement releasably adhering to a body part, the textile layer, which is disposed on an inner side adapted to contact the body part, is adhesive-free such that the adhesive bodies are configured to adhere to the body part and the textile layer is not configured to adhere to the body part.

2. The sensor as claimed in claim 1, wherein the carrier part has a hook and loop fastening element comprising a hook element having hooks and a loop element having loops.

3. The sensor as claimed in claim 2, wherein
the hook element is designed as a tongue which at one end is anchored between the foam layer and the lower part and at the other end of the tongue projects beyond the carrier part.

4. A The sensor as claimed in claim 2, wherein the loop element is formed by an outer side of the lower half which forms the outer side of the carrier part.

5. A medical sensor for measuring pulse, blood, tissue and/or skin parameters by means of electromagnetic waves in the transmission or reflection method, having a strip- and/or band-shaped carrier part which carries at least one transmitter element and at least one receiver element,
wherein the carrier part, on an inner side provided to make contact with a body part of a patient, has [at least] two adhesive bodies which are spaced apart from one another and during measurement adhere to the body part, where the rest of the inner side is designed to be essentially non-adhesive with respect to the body part;
wherein the carrier part has a first textile layer that forms the inner side of the carrier part, on which there is arranged a first layer of foamed material that can be elastically compressed in the direction of the thickness, on which there is arranged a second layer of foamed material that can be elastically compressed in the direction of the thickness, on which there is arranged a second textile layer that forms an outer side of the carrier part,
where the at least one transmitter element and the at least one receiver element are arranged between the layers of foamed material,
where the first textile layer and the first layer of foamed material have a transmitter opening and a receiver opening through which the at least one transmitter element emits waves during transmission and the at least one receiver element receives waves,
a first of the adhesive bodies covers the at least one transmitter element, the first adhesive body being disposed in the transmitter opening and not extending onto the inner side of the carrier part,
a second of the adhesive bodies covers the at least one receiver element, the second adhesive body being disposed in the receiver opening and not extending onto the inner side of the carrier part, and
the first and second adhesive bodies are permeable to the waves emitted by the at least one transmitter element.

6. The sensor as claimed in claim 5, wherein
the at least one transmitter element is arranged in the carrier part, the at least one transmitter element emits waves during measurement, through the first adhesive body that is disposed in the transmitter opening; and
the at least one receiver element is arranged in the carrier part, the at least one receiver element receives waves during measurement through the second adhesive body that is disposed in the receiver opening.

7. The sensor as claimed in claim 6, wherein
the first adhesive body adheres to the at least one transmitter element and releasably adheres to the body part, and
the second adhesive body adheres to the at least one receiver element and releasably adheres to the body art.

8. The sensor as claimed in claim 5, wherein the adhesive bodies consist of a gel-like adhesive compound.

9. The sensor as claimed in claim 5, wherein the adhesive bodies consist of an adhesive that is not hardened and does not harden during the service life of the sensor.

10. A The sensor as claimed in claim 5, wherein
the at least one transmitter element and the at least one receiver element are arranged between a first adhesive film and a second adhesive film,
the adhesive films are arranged between the layers of foamed material, and
the first adhesive film has a transmitter opening and a receiver opening.

11. A sensor for measuring pulse, blood, tissue and/or skin parameters by means of electromagnetic waves in the transmission or reflection method, having a strip- and/or band-shaped carrier part which carries at least one transmitter element and at least one receiver element,
wherein the at least one transmitter element and the at least one receiver element are arranged on the carrier part on a longitudinal center line of the carrier part and spaced apart from one another in the longitudinal direction of the carrier part;
wherein the carrier part has two lateral notches that lie opposite one another in the center, with respect to its longitudinal direction, between the at least one transmitter element and the at least one receiver element; and
wherein the carrier part, on an inner side provided to make contact with a body part of a patient, has at least two adhesive bodies which are spaced apart from one another and during measurement adhere to the body part, where the rest of the inner side is designed to be essentially non-adhesive with respect to the body part;
wherein the carrier part defines a transmitter well in which the transmitter element is disposed and a receiver well in which the receiver element is disposed;
the first adhesive body completely fills the transmitter well;
the second adhesive body completely fills the receiver well, and
the inner side of the carrier part is adhesive-free, such that only the first and second adhesive bodies adhere to the body part.

12. The sensor as claimed in claim 11, wherein the carrier part is designed to be elastically compressible in the direction of its thickness, such that the carrier part can be compressed at the time of application to the body part, such that restoring forces press the inner side of the carrier part, the first adhesive body and the second adhesive body against the body part.

13. The A sensor as claimed in claim 11, wherein the carrier part has a multilayer structure and, between two textile layers, one of which forms the inner side of the carrier part and the other of which forms an outer side of the carrier part, has at least one layer of foamed material that can be elastically compressed in the direction of the thickness.

14. The sensor as claimed in claims 13, wherein the layers of the multilayer carrier part are adhesively and/or thermally bonded to one another.

15. The sensor as claimed in claim 11, wherein a projection which sticks out to the side is formed on the carrier part, to which projection cables are attached which lead to the at least one transmitter element and to the at least one receiver element.

16. A medical sensor comprising:
   a carrier part having an inner surface adapted to contact a body part of a patient;
   a receiver recessed in a first well defined in said carrier part;
   a transmitter received in a second well defined in said carrier part;
   at least two adhesive bodies, wherein one adhesive body is disposed in the first well, covers the receiver, and is configured to adhere to the body part and another adhesive body is disposed in the second well, covers the transmitter, and is configured to adhere to the body part;
   wherein the receiver and the transmitter are spaced apart from one another; and
   wherein the inner surface of the carrier art is adhesive-free such that only the adhesive bodies adhere to the body part.

17. The medical sensor of claim 16, wherein said at least two adhesive bodies are comprised of a gel-like adhesive material which is transmissive to waves transmitted by the transmitter.

* * * * *